United States Patent
Kiss et al.

(10) Patent No.: US 9,364,823 B2
(45) Date of Patent: Jun. 14, 2016

(54) ACTIVATION AND USE OF HYDROALKYLATION CATALYSTS

(71) Applicant: ExxonMobil Chemical Patents Inc., Baytown, TX (US)

(72) Inventors: Gabor Kiss, Hampton, NJ (US); Christopher L. Becker, Manhattan, KS (US); Tan-Jen Chen, Kingwood, TX (US); Thomas E. Green, Hamilton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/424,832

(22) PCT Filed: Oct. 3, 2013

(86) PCT No.: PCT/US2013/063187
§ 371 (c)(1),
(2) Date: Feb. 27, 2015

(87) PCT Pub. No.: WO2014/074248
PCT Pub. Date: May 15, 2014

(65) Prior Publication Data
US 2015/0224493 A1    Aug. 13, 2015

Related U.S. Application Data

(60) Provisional application No. 61/712,980, filed on Oct. 12, 2012.

(51) Int. Cl.

| | |
|---|---|
| C07C 45/53 | (2006.01) |
| C07C 31/08 | (2006.01) |
| C07C 2/66 | (2006.01) |
| B01J 29/00 | (2006.01) |
| B01J 37/18 | (2006.01) |
| B01J 37/08 | (2006.01) |
| B01J 35/00 | (2006.01) |
| B01J 23/44 | (2006.01) |
| B01J 29/064 | (2006.01) |
| B01J 29/72 | (2006.01) |
| B01J 29/74 | (2006.01) |
| C07C 37/08 | (2006.01) |
| C07C 2/74 | (2006.01) |
| C07C 407/00 | (2006.01) |
| B01J 35/02 | (2006.01) |
| B01J 37/00 | (2006.01) |
| B01J 37/02 | (2006.01) |
| C07C 29/04 | (2006.01) |

(52) U.S. Cl.
CPC B01J 37/18 (2013.01); B01J 23/44 (2013.01); B01J 29/064 (2013.01); B01J 29/7276 (2013.01); B01J 29/7476 (2013.01); B01J 35/0006 (2013.01); B01J 35/023 (2013.01); B01J 35/026 (2013.01); B01J 37/0009 (2013.01); B01J 37/0201 (2013.01); B01J 37/08 (2013.01); C07C 2/66 (2013.01); C07C 2/74 (2013.01); C07C 29/04 (2013.01); C07C 37/08 (2013.01); C07C 45/53 (2013.01); C07C 407/00 (2013.01); *C07C 2101/14* (2013.01); *C07C 2529/70* (2013.01); *C07C 2529/74* (2013.01); *Y02P 20/52* (2015.11)

(58) Field of Classification Search
CPC .......... C07C 45/53; C07C 37/08; C07C 2/66; B01J 29/7476
USPC ........ 568/341, 798; 585/268, 467; 502/74, 85
See application file for complete search history.

(56) References Cited

U.S. PATENT DOCUMENTS

| | | |
|---|---|---|
| 3,760,017 A | 9/1973 | Arkell et al. |
| 3,760,018 A | 9/1973 | Suggitt et al. |
| 4,268,699 A | 5/1981 | Murtha et al. |
| 4,329,531 A | 5/1982 | Murtha et al. |
| 4,439,409 A | 3/1984 | Puppe et al. |
| 4,826,667 A | 5/1989 | Zones et al. |
| 4,954,325 A | 9/1990 | Rubin et al. |
| 5,053,571 A | 10/1991 | Makkee |
| 5,236,575 A | 8/1993 | Bennett et al. |
| 5,250,277 A | 10/1993 | Kresge et al. |
| 5,362,697 A | 11/1994 | Fung et al. |
| 6,037,513 A | 3/2000 | Chang et al. |
| 6,077,498 A | 6/2000 | Diaz Cabanas et al. |
| 6,720,462 B2 | 4/2004 | Kuhnle et al. |
| 6,756,030 B1 | 6/2004 | Jan et al. |

FOREIGN PATENT DOCUMENTS

| | | |
|---|---|---|
| EP | 0 293 032 | 11/1988 |
| EP | 0338734 | 7/1992 |
| WO | 97/17290 | 5/1997 |
| WO | 2009/025939 | 2/2009 |
| WO | WO2009/021604 | 2/2009 |
| WO | WO2009/128984 | 10/2009 |
| WO | WO2012/050751 | 4/2012 |

OTHER PUBLICATIONS

G. N. Koshel et al., "One-Step Hydrodimerization of Benzene to Phenylcyclohexane and Various Industrial Synthesis Processes Which Utilize This Method", USSR Academy of Sciences Publications, 1977. vol. 237, No. 1.
Lynn H. Slaugh et al., "*Hydrodimerization\* of Benzene to Phenylcyclohexane over Supported Transition Metal Catalysts*", J. Catal. 13 (4) (1969) pp. 385-396.

*Primary Examiner* — Sikarl Witherspoon
(74) *Attorney, Agent, or Firm* — Siwen Chen; Stephen A. Baehl

(57) ABSTRACT

In a process for activating a hydroalkylation catalyst, a catalyst precursor comprising a solid acid component and a compound of a hydrogenation metal is heated at a heating rate of less than 50° C./hour in the presence of hydrogen to an activation temperature in a range from 100° C. to 260° C. and then the heated catalyst precursor is treated with hydrogen for a duration effective to reduce at least a portion of the metal compound to an elemental form.

17 Claims, No Drawings

US 9,364,823 B2

ACTIVATION AND USE OF HYDROALKYLATION CATALYSTS

PRIORITY CLAIM

This application is a National Stage Application of International Application No. PCT/US2013/063187 filed Oct. 3, 2013, which claims priority to U.S. Provisional Application Ser. No. 61/712,980 filed Oct. 12, 2012, the disclosures of which are fully incorporated herein by reference.

FIELD

The present invention relates to the activation of hydroalkylation catalysts and to the use of the activated catalysts in producing cycloalkylaromatic compounds, in particular cyclohexylbenzene.

BACKGROUND

The production of cycloalkylaromatic compounds, such as cyclohexylbenzene, is a commercially important process since the latter has utility as a solvent and a source of chemical intermediates, such as, for example, phenol and cyclohexanone, which are important intermediates in the production of, for example, phenolic resins, bisphenol A, ε-caprolactam, adipic acid and plasticizers.

One process for producing cycloalkylaromatic compounds, such as cyclohexylbenzene, involves the catalytic hydroalkylation of aromatic compounds, such as benzene, over a bifunctional catalyst. The bifunctional catalyst may comprise an alkylation component comprising a solid acid, such as a molecular sieve, or amorphous silica-alumina, or any suitable solid acid, and a hydrogenation component, such as a Group 8-10 metal. The hydrogenation component may be introduced into the catalyst by impregnation with a solution of a water-soluble salt of the relevant Groups 8-10 metal. The catalyst may also comprise promoters, such as, for example, alkali or alkali-earth metals, Group 3 or Group 4 metals, Zn, Sn, Re, halogens, etc. The impregnated catalyst is then dried and calcined in air, typically at a temperature of 250° C. to 550° C. To bring the catalyst into its active form, the catalyst is then heated in the presence of hydrogen primarily to reduce the hydrogenation component to its active metallic form. This activation process may also serve to remove adsorbed water that would inhibit the alkylation reaction.

An example of such a process is described in, for example, U.S. Pat. No. 3,760,017, which discloses a method for the catalytic hydroalkylation of benzene to cyclohexylbenzene using a bifunctional catalyst followed by the conversion of the cyclohexylbenzene to cyclohexanone and phenol by air oxidation and acid decomposition. The bifunctional catalyst comprises a metal in Groups 8-10 of the Periodic Table selected from the group consisting of cobalt, nickel and palladium and an acidic oxide support consisting essentially of a substantially alkali metal-free mixture of about 5 to 60 percent by weight of a crystalline zeolite, such as zeolite Y, and about 95 to 40 percent by weight of a silica-alumina cracking catalyst. The bifunctional catalyst is produced by impregnating the support with a solution of the desired hydrogenation metal(s) followed by calcining in an oxidizing atmosphere to convert the hydrogenating component to the oxide form. The catalyst is then reduced, by contact with hydrogen at a temperature of 400° F. to 1200° F. (204° C. to 649° C.).

A further process for the catalytic hydroalkylation of benzene is described in U.S. Pat. No. 6,037,513, in which the bifunctional catalyst comprises a crystalline inorganic oxide material having alkylation activity and an X-ray diffraction pattern including d-spacing maxima at 12.4±0.25, 6.9±0.15, 3.57±0.07, and 3.42±0.07 Angstrom and a hydrogenation metal selected from palladium, ruthenium, nickel, and cobalt. In the Examples, the catalyst is produced by impregnating the crystalline inorganic oxide material with an aqueous solution of a metal salt and then treating the impregnated oxide material with 50 cc/min of flowing hydrogen for 2 hours at 300° C. and 1 atm pressure. Although not stated in the '513 patent, this hydrogen treatment activates the catalyst by reducing the metal salt to its elemental form.

In WO 2012/050751, a process of the hydrogen activation of a catalyst is conducted at a temperature below 250° C., such as at temperature in a range from 0 to 200° C. Lowering the activation temperature is found to increase the cyclohexylbenzene selectivity of the catalyst. In the Examples, the catalyst is produced by impregnating the bound crystalline inorganic oxide material with an aqueous solution of palladium chloride and then activating the impregnated oxide material in the hydroalkylation reactor with a flow of 47-80 microliter/min benzene and 15-25 sccm hydrogen while the reactor temperature is ramped to 145° C. at 1° C./minute. In some cases, the hydrogen activation is preceded by a drying step where the catalyst is heated at a temperature below 200° C., in the presence of a dry gas, such as nitrogen, to reduce the water level of the catalyst to less than 15 wt %, such as 1 wt % to 12 wt %.

SUMMARY

According to the present invention, it has now been found that the activation of hydroalkylation catalysts, such as those disclosed in U.S. Pat. No. 6,037,513, can be simplified, generally without reduction in the activity or selectivity of the final catalyst, by a combination of a low heating rate and a low final temperature during the activation process. In particular, activation is achieved by heating the initial catalyst in the presence of flowing hydrogen to an activation temperature in a range from 100° C. to 260° C. at a slow heating or ramp rate of less than 50° C./hour and then holding the catalyst at or near this activation temperature in flowing hydrogen for a sufficient period of, e.g., 12 hours. While the process is not fully understood, the slow heating rate is believed to reduce the rate of water release from the catalyst during activation, which is in turn believed to enhance the activation process. In addition, since heating of the catalyst may be achieved by the activation gas, reducing the catalyst heating rate allows the hydrogen flow rate during activation to be reduced, which reduces the gas handling capacity required at start-up and the gas handling costs.

In a first aspect, the invention resides in a process for activating a hydroalkylation catalyst, the process comprising:

(a) providing a hydroalkylation catalyst precursor comprising a solid acid component and a compound of a hydrogenation metal;

(b) heating the catalyst precursor at a heating rate of less than 50° C./hour in the presence of hydrogen to an activation temperature in a range from 100° C. to 260° C.; and (c) treating the heated catalyst precursor with hydrogen in a temperature range from 50° C. below the activation temperature to the activation temperature for a duration to reduce at least a portion of the metal compound to an elemental form.

In a second aspect, the invention resides in a process for producing a cycloalkylaromatic compound, the process comprising: contacting an aromatic compound and hydrogen with a catalyst prepared using a process according to the first aspect in a hydroalkylation reactor under hydroalkylation conditions effective to convert at least part of the aromatic compound to a cycloalkylaromatic compound.

In some embodiments, the heating rate in step (b) is less than 30° C./hour, such as less than 20° C./hour, for example from 1 to 10° C./hour.

In some embodiments, the activation temperature is less than or equal to 240° C., such as in a range from 100° C. to 240° C.

In some embodiments, hydrogen is supplied during steps (b) and (c) at a gas hourly space velocity (GHSV) of less than 1000 hour$^{-1}$, such as less than 800, 600, 500, 400, 300, 250, 200, or even 150, hour$^{-1}$.

In some embodiments, the treating step (c) is conducted at a hydrogen partial pressure in a range from about 0.1 bar to about 100 bar (10 kPa to about 10,000 kPa), such as in a range from about 1 bar to about 20 bar (100 kPa to about 2,000 kPa), for a duration of up to 24 hours, such as about 0.5 to about 24 hours.

In one embodiment, the aromatic compound is benzene and the cycloalkylaromatic compound is cyclohexylbenzene.

In a further aspect, the invention resides in a process for producing a phenol and cyclohexanone, the process comprising:

(a1) providing a hydroalkylation catalyst precursor comprising a solid acid component and a compound of a hydrogenation metal;

(a2) heating the catalyst precursor at a heating rate of less than 50° C./hour in the presence of hydrogen to an activation temperature in a range from 100° C. to 260° C.;

(a3) treating the heated catalyst precursor with hydrogen in a temperature range from 50° C. below the activation temperature to the activation temperature for a duration to at least reduce a portion of the metal compound to an elemental form;

(a) contacting benzene and hydrogen with a catalyst prepared by a process comprising steps (a1) to (a3) in a hydroalkylation reactor under hydroalkylation conditions effective to convert at least part of the benzene to cyclohexylbenzene;

(b) oxidizing at least part of the cyclohexylbenzene produced in step (a) to produce cyclohexylbenzene hydroperoxide; and (c) cleaving at least part of the cyclohexylbenzene hydroperoxide produced in step (b) to produce phenol and cyclohexanone.

DETAILED DESCRIPTION

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, individual steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydroalkylation catalyst" include embodiments where one, two or more such catalysts are used, unless specified to the contrary or the context clearly indicates that only one hydroalkylation catalyst is used. Likewise, "a hydrogenation metal" should be interpreted to include one, two or more such metals unless specified or indicted by the context to mean only one specific metal.

As used herein, "wt %" means percentage by weight, "vol %" means percentage by volume, "mol %" means percentage by mole, "ppm" means parts per million, and "ppm wt," "wt ppm" and "wppm" are used interchangeably to mean parts per million on a weight basis. All "ppm" as used herein are ppm by weight unless specified otherwise. All concentrations herein are expressed on the basis of the total weight of the composition in question. All ranges expressed herein should include both end points as two specific embodiments unless specified or indicated to the contrary.

As used herein, "activation temperature" is the highest temperature (Tmax) the catalyst precursor has been exposed to during the activation process. The term "around the activation temperature" means within the range from Tmax–50° C. to Tmax.

Described herein is a process for activating a catalyst useful in the hydroalkylation of benzene and substituted benzenes, particularly alkyl-substituted benzenes, for example ethylbenzene, toluene, and xylenes, to produce cycloalkylaromatic compounds. In one embodiment, the activated catalyst is employed in the hydroalkylation of benzene to produce cyclohexylbenzene, which can then be oxidized to produce cyclohexylbenzene hydroperoxide, which in turn is cleaved to produce phenol and cyclohexanone. The ensuing description will therefore focus on this integrated process.

Preparation and Activation of the Hydroalkylation Catalyst

The hydroalkylation catalyst employed in the present process is a bifunctional catalyst comprising a solid acid component and a hydrogenating metal function, optionally together with an amorphous inorganic oxide support component.

Suitable solid acid components for the catalyst include mixed metal oxides, for example, tungstated zirconia, and molecular sieves, for example, zeolite beta, zeolite X, zeolite Y, mordenite and zeolites of the MWW framework type (see "Atlas of Zeolite Framework Types", Fifth edition, 2001). Molecular sieves of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. In one practical embodiment, the molecular sieve of the MWW framework type is selected from MCM-22 and MCM-49.

Any known hydrogenating metal function can be employed in the hydroalkylation catalyst, although suitable metals include palladium, platinum, ruthenium, iron, rhenium, rhodium, osmium, iridium, nickel, zinc, tin, and cobalt, with palladium being particularly advantageous. In some embodiments, the amount of hydrogenating metal function present in the catalyst is in a range from about 0.01 wt % to about 10 wt %, such as in a range from about 0.05 wt % to about 5 wt %, of the catalyst. In one embodiment, where the solid acid component of the catalyst is an aluminosilicate molecular sieve, the molar ratio of the aluminum in the molecular sieve to the hydrogenating metal is in a range from about 1.5 to about 1500, for example in a range from about 30 to about 750, or in a range from 75 to 750, such as in a range from about 30 to about 300.

The hydrogenating metal may be directly supported on the solid acid component by, for example, impregnation or ion exchange, or can be supported on the amorphous inorganic oxide component, or both. In one embodiment, at least 50 wt %, for example at least 75 wt %, or substantially all of the hydrogenating metal is supported on an amorphous inorganic oxide support component separate from but composited with the solid acid component. By supporting the hydrogenating metal on the amorphous inorganic oxide support, the activity of the catalyst and its selectivity to cyclohexylbenzene, dicyclohexylbenzene, and tricyclohexylbenzene in the hydroalkylation reaction are increased as compared with an equivalent catalyst in which the hydrogenating metal function is supported directly on the solid acid component.

The amorphous inorganic oxide support employed in such a composite hydroalkylation catalyst is not narrowly defined provided it is stable and inert under the conditions of the hydroalkylation reaction. Suitable inorganic oxides include oxides of Groups 2, 3, 4, 5, 13, and 14 of the Periodic Table of Elements. Examples for suitable and widely available amorphous inorganic oxides include, for example, alumina, silica, silica-alumina, titania, and/or zirconia, etc. As used herein, the numbering scheme for the Periodic Table Groups is as disclosed in Chemical and Engineering News, 63(5), 27 (1985).

Where the hydrogenating metal is deposited on the inorganic oxide support, this is conveniently effected by impregnation with a solution of a salt of the desired metal, before the metal-containing inorganic oxide is composited with said solid acid component. In some embodiments, the catalyst composite is produced by co-pelletization, in which a mixture of the solid acid component and the metal-containing inorganic oxide is formed into pellets at high pressure (e.g., about 350 kPa to about 350,000 kPa), or by co-extrusion, in which a slurry of the solid acid component and the metal-containing inorganic oxide, optionally together with a separate binder, are forced through a die. If necessary, additional hydrogenating metal can subsequently be deposited on the resultant catalyst composite.

In some other embodiments, the crystalline solid acid is first extruded with the amorphous oxide as a binder, then the metal is impregnated into the extrudate. In this case, the impregnation conditions can be adjusted such that the metal is preferentially associated with the amorphous oxide component of the extrudate.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

Immediately after incorporating the hydrogenating metal function into the molecular sieve/inorganic oxide composite, the hydrogenation metal is normally in an oxidized form and so, before being employed in a hydroalkylation process, the resultant catalyst precursor must be activated to convert at least some of the metal to its zero-valent elemental state. The activation process is conducted by heating the catalyst precursor in the presence of hydrogen, in certain embodiments in the same reactor as that used for the subsequent hydroalkylation step. However, if desired, the activation may be conducted in one or more separate reactors and the activated catalyst is subsequently transferred to the hydroalkylation reactor.

The activation is conducted during the temperature ramping up step and the temperature holding step around an activation temperature, Tmax, defined above. The activation temperature can be in a range from a lower temperature Tl ° C. to a higher temperature Th ° C., where Tl may be, e.g., 100, 110, 120, 130, 140, 150, 160, 170, 180, 190, 200, 210; and Th may be, e.g., 160, 170, 180, 190, 200, 210, 220, 230, 240, 250 and 260, as long as Tl<Th. The catalyst precursor is heated to the target activation temperature in the presence of hydrogen from some initial lower temperature, in some embodiments ambient temperature (about 25° C.), at a heating rate of less than 50° C., such as less than 30° C./hour, for example less than 20° C./hour, for example in a range of 1 to 10° C./hour.

The activation (both the ramping up of the temperature and heating at or around the target activation temperature) is performed in the presence of a flowing hydrogen-containing gas that advantageously passes through the catalyst bed being activated. Although higher feed rates could be applied, the hydrogen feed flow rate (net of other gases present in the activation gas) is advantageously less than 1000 hour$^{-1}$, or less than 800, 600, 500, 400, 300, 250, 200, or even 150 hour$^{-1}$ GHSV, while the hydrogen partial pressure in the activation gas feed is higher than 0.1 bar (10 kPa), or 0.2 bar (20 kPa), or 0.5 bar (50 kPa), or 0.8 bar (80 kPa), or 1.0 bar (100 kPa), or 3 bar (300 kPa), or 5 bar (500 kPa), or 10 bar (1,000 kPa), or 15 bar (1,500 kPa), or 20 bar (2,000 kPa). In certain embodiments, the hydrogen partial pressure is in a range from about 0.1 bar to about 100 bar (about 10 kPa to 10,000 kPa).

The activation gas can be essentially pure hydrogen or the hydrogen can be diluted with a gas that is inert under the activation conditions, such as, for example, nitrogen or methane, thus the total pressure of the feed gas could be above that of the partial pressure of the feed hydrogen described above. The use of inert gas diluents may be advantageous in that the cost of the feed gas could be lower and/or because the heat capacity of the activation gas could be higher thus facilitating the heat up of the catalyst bed if the heat is delivered by preheating the activation gas. Advantageously, the catalyst is activated in the hydroalkylation reactor and the total pressure applied during catalyst activation by the currently disclosed process is at or below that used in the hydroalkylation process. Thus, in certain embodiments, the total reactor pressure during activation is at or below 100 bar (10,000 kPa), or 50 bar (5,000 kPa), or 25 bar (2,500 kPa), or 20 bar (2,000 kPa), or 15 bar (1,500 kPa), or even below 10 bar (1,000 kPa).

The catalyst precursor is held around the activation temperature in flowing hydrogen-containing gas for a duration in a range from D1 hours to D2 hours sufficient to reduce the hydrogenation metal component to an elemental form. The duration includes the following: (i) the time required for the initial heating of the catalyst precursor from Tmax−50° C. to Tmax; (ii) the time for holding the temperature of the catalyst precursor in the range from Tmax−50° C. to Tmax after Tmax has been reached. It should be noted that some temperature fluctuation during the temperature holding step is permitted. Non-limiting examples of D1 may be 0.5, 1, 2, 3, 4, 5, 6, 7, 8, 9, 10, 12, 14, 16, 18, 20; and non-limiting examples of D2 may be 5, 6, 7, 8, 9, 10, 12, 14, 16, 18, 20, 24, 28, 32, 36, 40, 44 and 48, as long as D1<D2. Lower temperatures tend to require longer hold times due to slower activation. At 260° C. maximum activation hold times of 0.5 to 24 hours may be sufficient in certain embodiments, while at 200° C. maximum activation temperature, longer hold times may be needed, e.g., in a range from Ht1 hours to Hth hours, where Htl may be, e.g., 4, 6, 8, 10, 12, 14, 16, 18, 20, 22, or 24; and Hth may be, e.g., 12, 14, 16, 18, 20, 22, 24, 26, 28, 30, 32, 36, 40, 44, or 48, as long as Htl<Hth.

During the heating step (b) and the treating step (c), the contact of $H_2$ with the catalyst precursor results in the reduction of at least part of the metal compound into metallic, elemental form. At the highest temperature at or around the activation temperature, the reaction rate of the reaction of $H_2$ and the metal compound is normally the highest. Thus, it is highly desirable that at the end of the treating period where the temperature is held around the activation temperature, a great majority, such as at least 80 wt %, or at least 90 wt %, or at least 95 wt %, or at least 98 wt %, or at least 99 wt %, or at least 99.5 wt %, or at least 99.9 wt %, of the metal compound has been reduced to elemental form. In the case where the metal compound is $PdCl_2$, the following reaction occurs during activation:

$$PdCl_2 + H_2 \rightarrow Pd + 2HCl.$$

In the case where the metal compound is $PtO_2$, the following reaction occurs during activation:

$$PtO_2 + 2H_2 \rightarrow Pt + 2H_2O.$$

The flowing activation gas would purge the HCl and $H_2O$ produced in the reductive reaction. Thus, it is highly desired that the activation gas is substantially dry, e.g., it may contain $H_2O$ at a concentration of at most AA ppm by volume, where AA can be 500, 400, 300, 200, 100, 80, 60, 50, 40, 20, 10, or even 5 in various embodiments of the process of the present disclosure.

At the end of the step (c), the activated catalyst can be put into use directly if the activation is carried out in situ in a reactor where it will be used, such as a hydroalkylation reactor for producing cyclohexylbenzene from benzene and $H_2$. Alternatively, the activated catalyst may be transferred from an activation vessel to the reactor. In either case, it is highly desired that the exposure of the catalyst to an oxidative atmosphere, such as air, is minimized, especially at an elevated temperature. To that extent, an in-situ activated catalyst prepared according to the present disclosure may be protected by a flowing inert or reducing atmosphere, such as a $H_2$-containing atmosphere, a $CH_4$-containing atmosphere, pure $N_2$, and the like, inside the reactor before being put into service. If the activated catalyst needs to be cooled down upon activation and/or stored before being put into its intended use, it is desired that the cooling and/or storing are carried out in the presence of a reductive or inert atmosphere, such as a $H_2$-containing atmosphere, a $CH_4$-containing atmosphere, pure $N_2$, and the like.

Hydroalkylation Process

Following the activation process described above, the resultant hydroalkylation catalyst can be employed in the desired hydroalkylation reaction to convert an aromatic compound to a cycloalkylaromatic compound and, in the particular embodiment described herein, to convert benzene to cyclohexylbenzene (CHB) according to the following reaction:

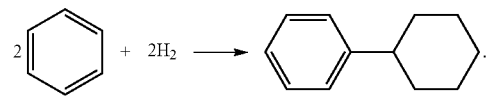

Any commercially available benzene feed can be used in the hydroalkylation step, but desirably the benzene has a purity level of at least 80 wt %, or at least 85 wt %, or at least 90 wt %, or at least 95 wt %, or even at least 99 wt %. In general, the benzene feed can be diluted with inert components, such as paraffins, without preventing the desired chemical transformation, but excessive amounts of diluents tend to increase process cost, and so are not advantageous.

Similarly, although the source of hydrogen is not critical, it may be desirable that the hydrogen is at least 70 vol % pure, or at least 75 vol % pure, or at least 80 vol % pure, or at least 85 vol % pure, or at least 90 vol % pure, or at least 95 vol % pure at least 99 vol % pure. Advantageously, the feed hydrogen contains less than 50 vol % inert diluents, but hydrogen feeds with higher concentration of inert diluents can also be used to achieve meaningful conversion of the benzene feed.

In some embodiments, the total feed to the hydroalkylation process contains less than 1000 ppm, such as less than 500 ppm, for example less than 100 ppm, water. In addition, the total feed to the hydroalkylation process should be substantially free of nitrogen compounds and sulfur compounds, i.e., contain less than 100 ppm, such as less than 10 ppm, for example less than 1 ppm, for example less than 0.1 ppm, for example less than 0.01 ppm, for example less than 0.001 ppm, sulfur, and less than 10 ppm, such as less than 1 ppm, for example less than 0.1 ppm, for example less than 0.01 ppm, for example less than 0.001 ppm nitrogen in the form of a nitrogen-containing compound. For the purpose of the present disclosure, nitrogen gas ($N_2$) is not considered as a nitrogen-containing compound due to the inert nature of $N_2$ in the hydroalkylation reaction.

Hydrogen can be supplied to the hydroalkylation step over a wide range of values, and in certain embodiments is arranged such that the molar ratio of hydrogen to benzene in the hydroalkylation feed is in a range from about 0.15:1 to about 15:1, such as in a range from about 0.4:1 to about 4:1, for example in a range from about 0.4 to about 0.9:1. Advantageously, the hydrogen content in the feed is below that necessary to achieve 100% conversion of benzene to cyclohexane, or even below that is necessary to achieve 100% conversion of benzene to cyclohexylbenzene to increase hydroalkylation selectivity and decrease the potential of temperature runaway.

In addition to benzene and hydrogen, a diluent, which is substantially inert under hydroalkylation conditions, may be supplied to the hydroalkylation reaction. In certain embodiments the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of useful diluents are decane and cyclohexane. Cyclohexane is a more preferred diluent in certain embodiments since it is an unwanted by-product of the hydroalkylation reaction.

Although the amount of diluent is not narrowly defined, in certain embodiments the diluent present in the liquid hydroalkylation feed is less than 90 wt %, or less than 50 wt %, or less than 25 wt %, or less than 10 wt %, or less than 5 wt %, or less than 1 wt % of the feed.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen may be introduced to the reaction in stages. Suitable reaction temperatures are in a range from about 100° C. to about 400° C., such as in a range from about 125° C. to about 250° C., while suitable reaction pressures are in a range from about 100 kPa to about 7,000 kPa (absolute), such as in a range from about 500 kPa to about 5,000 kPa (absolute).

Although the hydroalkylation reaction using an MCM-22 family zeolite catalyst activated by the process described herein is highly selective towards cyclohexylbenzene, the effluent from the hydroalkylation reaction will contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene may be effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction may be conducted under at least partial liquid phase conditions, which suitably include a temperature of about 100° C. to about 300° C., a pressure of about 800 kPa to about 3500 kPa, a weight hourly space velocity of about 1 hour$^{-1}$ to about 10 hour$^{-1}$ on total feed, and a benzene/dicyclohexylbenzene weight ratio about of 1:1 to about 5:1.

Dealkylation or cracking may be also effected in a reactor separate from the hydroalkylation reactor, such as a reactive distillation unit, at a temperature of about 150° C. to about 500° C. and a pressure of 15 psig to 500 psig (200 kPa gauge to 3550 kPa gauge) over an acid catalyst such as an aluminosilicate, an aluminophosphate-based material, a silicoaluminophosphate, amorphous silica-alumina, an acidic clay, a mixed metal oxide, such as WO$_x$/ZrO$_2$, phosphoric acid, sulfated zirconia and mixtures thereof. In certain embodiments, the acid catalyst includes at least one aluminosilicate, aluminophosphate-based material or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction may be in a range from 0 to about 0.9, such as in a range from about 0.01 to about 0.5. Similarly, although the dealkylation reaction can be conducted in the absence of added hydrogen, hydrogen may be introduced into the dealkylation reactor to assist in coke reduction. Suitable hydrogen addition rates are such that the molar ratio of hydrogen to poly-alkylated aromatic compound in the total feed to the dealkylation reactor is in a range from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst may comprise (a) a support; (b) a hydrogenation-dehydrogenation component and (c) an inorganic promoter. Conveniently, the support (a) is selected from the group consisting of silica, a silicate, an aluminosilicate, zirconia, and carbon nanotubes, and desirably comprises silica. Suitable hydrogenation-dehydrogenation components (b) comprise at least one metal selected from Groups 6 to 10 of the Periodic Table of Elements, such as platinum, palladium and compounds and mixtures thereof. In some embodiments, the hydrogenation-dehydrogenation component is present in an amount in a range from about 0.1 wt % to about 10 wt % of the catalyst. A suitable inorganic promoter (c) comprises at least one metal or compound thereof selected from Group 1 of the Periodic Table of Elements, such as a potassium compound. In some embodiments, the promoter is present in an amount in a range from about 0.1 to about 5 wt % of the catalyst. Suitable dehydrogenation conditions include a temperature of about 250° C. to about 500° C., an absolute pressure of about atmospheric to about 500 psig (100 kPa to 3550 kPa), a weight hourly space velocity of about 0.2 hour$^{-1}$ to 50 hour$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst may be an acid catalyst, such as an aluminosilicate zeolite, and especially faujasite and the treatment is conducted at a temperature of about 100° C. to about 350° C., such as about 130° C. to about 250° C., for a duration of about 0.1 to about 3 hours, such as about 0.1 to about 1 hour. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

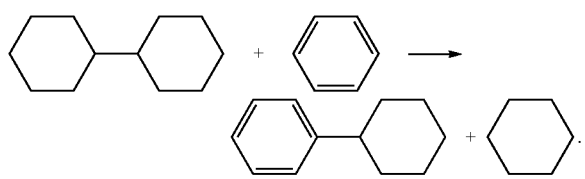

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above can be separated from the reaction effluent(s) by conventional methods. In the preferred embodiment, where the cyclohexylbenzene is an intermediate product in the production of phenol, the cyclohexylbenzene is fed to the oxidation reaction described in more detail below.

Cyclohexylbenzene Oxidation

In order to convert the cyclohexylbenzene into phenol, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to remove particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Desirably, the catalyst is N-hydroxyphthalimide. Another suitable catalyst is N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. In some embodiments, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene. The use of such oxidation catalysts in the manner disclosed herein conveniently facilitates a high selectivity to the desired cyclohexyl-1-phenyl-1-hydroperoxide, although other hydroperoxides may also be formed in varying quantities and be present in the oxidation effluent.

Suitable conditions for the oxidation step include a temperature in a range from about 70° C. to about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, e.g., by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

In some embodiments, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation effluent. In certain embodiments, the oxidation effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation effluent. The oxidation effluent may further comprise imide catalyst and unreacted cyclohexylbenzene. For example, the oxidation effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation effluent.

At least a portion of the oxidation effluent may be subjected to a cleavage reaction, with or without undergoing any prior separation or treatment. For example, all or a fraction of the oxidation effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passing through an adsorbent, such as a 3 Å molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

In certain embodiments, the acid catalyst used in the cleavage reaction is at least partially soluble in the cleavage effluent, is stable at a temperature of at least 185° C. and has a lower volatility (higher normal boiling point) than cyclohexylbenzene. In some embodiments, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage effluent contains at least 50 weight-parts-per-million (wppm) and no greater than 5000 wppm of the acid catalyst, or at least 100 wppm to no greater than 3000 wppm, or at least 150 wppm to and no greater than 2000 wppm of the acid catalyst, or at least 300 wppm and no greater than 1500 wppm of the acid catalyst, based upon total weight of the cleavage effluent.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage effluent may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2-pentanone, 3-pentanone, cyclohexanone, and methylcyclopentanone. The preferred polar solvent is phenol and/or cyclohexanone recycled from the cleavage product after cooling. In certain embodiments, the polar solvent is added to the cleavage effluent such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 w % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical induced conversion of the cyclohexylbenzene hydroperoxide to undesired products such as hexanophenone and phenylcyclohexanol.

In various embodiments, the cleavage effluent includes cyclohexylbenzene in an amount of at least 50 wt %, or at least 60 wt %, or at least 65 wt %, or at least 70 wt %, or at least 80 wt %, or at least 90 wt %, based upon total weight of the cleavage effluent.

In certain embodiments, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage effluent is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone in substantially equimolar proportions. These can be recovered from the cleavage effluent by methods known in the art.

The invention will now be more particularly described with reference to the following non-limiting Examples.

In the Examples, a series of hydroalkylation tests were performed in a down-flow 0.5" (12.7 mm) diameter stainless steel fixed bed reactor that was equipped with a three-point thermocouple positioned at the center of the reactor tube. The 4.5" (114 mm) long catalyst bed was positioned to ensure that three thermocouples (placed 2 inches (5 cm) apart) measured the temperatures at the inlet, outlet and the center of the catalyst bed. In order to reduce the volumetric heat release and thus to afford more isothermal operations, the catalyst was diluted with quartz. The diluent also enhanced the even distribution of the reactants in the catalyst bed. Neat quartz was used at either side of the catalyst bed. The quartz served to preheat and evenly distribute the feed at the feed inlet side and to hold the catalyst bed at the exit side, the latter of which was at the bottom of the reactor (downflow).

The reactor was encased in a 6 inches (15 cm) long and 1 inch (2.5 cm) diameter brass sleeve that was centered along the catalyst bed to improve its temperature control. Housed in the brass sleeve were the three thermocouples positioned at the two ends and the center of the catalyst bed. The reactor was heated by a three-zone clam-shell electrical furnace. During steady-state operations, the temperatures of the three furnace zones were controlled by utilizing the feedback from the three thermocouples in the brass sleeve of the reactor. The catalyst bed temperatures at the three thermocouples were typically within 2° C. of the set value. The reported reaction temperatures ($T_{rxn}$) were calculated as the weighted average of the three thermocouple measurements ($T_{inlet}$, $T_{middle}$, $T_{outlet}$) by the following formula:

$$T_{rxn}=(T_{inlet}+2T_{middle}+T_{outlet})/4.$$

The catalysts in all experiments nominally comprised of 0.15 wt % Pd supported on alumina-bound MCM-49 (alumina/MCM-49 of 20/80 wt/wt). The catalyst was made by first co-extruding $Al_2O_3$ with the molecular sieve, followed by impregnation using a $PdCl_2$ solution, and then calcination. The catalyst was received in its calcined form as 1/20" (1.27 mm) extrudate and was stored in closed plastic bottles. Before charging to the reactor, the catalyst extrudates were broken up and sized to a length/diameter (L/D) ratio of near one (14-20 mesh) to afford the reactor beds with proper hydrodynamics. As mentioned above, the catalyst was also diluted with quartz that on the one hand reduced volumetric catalyst charge and thus volumetric heat release while also improving the desired plug-flow characteristic of the reactant stream passing through the catalyst bed.

In an exemplary hydroalkylation test, 2 g of 14-20 mesh catalyst diluted with 6 g quartz was charged into the reactor. The moisture content of the as-loaded catalyst was nominally 12 wt %, thus the dry catalyst load was 1.76 g. After pressure testing, the catalyst was activated at 50 psig (345 kPa gauge) in flowing pure hydrogen. The hydrogen treatment was finished by letting the catalyst cool down to near the hydroalkylation temperature (145° C.) while keeping the pressure and hydrogen flow rate unchanged. The catalyst then was brought on hydroalkylation stream by first increasing the pressure to 165 psig (1138 kPa gauge), then reducing the hydrogen flow rate to 18 sccm and introducing benzene at 1 mL/min flow rate. This condition was maintained for 1 hour to ensure that the catalyst bed was properly wetted after which the benzene flow rate was reduced to 0.096 mL/min corresponding to a nominal 0.7 mol $H_2$/mol benzene feed composition and 2.5 weight benzene/weight catalyst hour$^{-1}$ (or 2.5 hour$^{-1}$) weight hourly space velocity (WHSV) on an as-loaded basis (i.e., catalyst with a nominal moisture content of 12 wt %).

After letting the reactor line out for about 6 hours, the product effluent was periodically directed to a chilled knock out vessel held at about 5° C. and liquid samples were collected and then analyzed by a gas chromatography equipped with a flame-ionization detector (FID). The response factors for the various product components were determined either using blends of authentic samples or by using factors published in the J. of Gas Chromatography in February 1967, p. 68 by W. A. Dietz. Calibrations were checked by analyzing gravimetrically prepared calibration blends. Benzene conversion and product selectivity were determined from the normalized FID areas by applying the calibration response factors.

Example 1 (Comparative)

2 g of a hydroalkylation catalyst comprising 0.15 wt % Pd on alumina/MCM49 20/80 wt/wt was sized and loaded into the reactor as described above. The catalyst was activated by ramping its temperature at 60° C./hour heating rate to 300° C. and holding it there for 2 hours in 2028 GHSV of flowing hydrogen at 3.44 bar (50 psig, 344 kPag) total pressure. Other details of the experimental procedure and the reactor were as described above. This reference case was established by running two experiments (A and B) parallel at identical conditions. As the results in Table 1 indicate, the catalyst yielded 35%-37% benzene conversion with 79% cyclohexylbenzene selectivity.

TABLE 1

| | Activation | | | Hydroalkylation | |
|---|---|---|---|---|---|
| Run No. | At TOS (Hour) | Maximal Temperature (° C.) | At TOS (Hour) | Benzene Conversion (%) | Cyclo-hexylbenzene Selectivity (%) |
| A | 0 | 300 | 2.2 | 285 | 35 | 79 |
| B | 0 | 300 | 2.2 | 290 | 37 | 79 |

TOS = time on stream

Example 2

As in Example 1, 2 g of a hydroalkylation catalyst comprising 0.15 wt % Pd on alumina/MCM49 20/80 wt/wt was sized and loaded into the reactor as described above. The catalyst was activated by ramping its temperature at 5 or 20° C./hour heating rate to 240° C. and holding it there for 4-13 hours in flowing hydrogen at 3.44 bar (50 psig, 344 kPag) total pressure. Two hydrogen flow rates (2028/hour and 120/hour GHSV) were applied for catalyst activation and the results are summarized in Table 2.

A comparison of the results from Examples 1 and 2 demonstrates that the currently disclosed catalyst activation process, with a low activation temperature and a low heating rate, can afford essentially the same catalyst activity and selectivity as was obtained by the prior art high temperature/high heating rate catalyst activation process. Thus, according to the present disclosure, the catalyst can be activated by using a $H_2$-containing activation gas at a lower flow rate and lower temperature where the catalyst precursor is heated primarily by the activation gas. This can be highly desirable due to the reduced cost and complexity.

TABLE 2

| Temperature | | Hold Time | Hydrogen | | Benzene | Cyclohexylbenzene |
| | | | GHSV | | | |
| Heating Rate (° C./hour) | Maximal (° C.) | at Maximal Temperature (Hour) | (volume $H_2$/volume catalyst/hour) | Flow (sccm/g catalyst) | Conversion (%) | Selectivity (%) |
| | | | | | @2.5 hour$^{-1}$ WHSV | |
| 5 | 240 | 12.5 | 2028 | 84.4 | 37 | 77 |
| 5 | 240 | 13.0 | 120 | 5.0 | 36 | 77 |

TABLE 2-continued

| Temperature | | Hold Time | Hydrogen GHSV | | Benzene | Cyclohexylbenzene |
|---|---|---|---|---|---|---|
| Heating Rate | Maximal | at Maximal Temperature | (volume H$_2$/volume | Flow (sccm/g | Conversion @2.5 hour$^{-1}$ | Selectivity WHSV |
| (° C./hour) | (° C.) | (Hour) | catalyst/hour) | catalyst) | (%) | (%) |
| 20 | 240 | 11.5 | 120 | 5.0 | 38 | 76 |
| 5 | 240 | 3.8 | 120 | 5.0 | 37 | 76 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. The contents of all references cited herein are incorporated by reference in their entirety.

Non-limiting embodiments of the processes of the present disclosure include:

E1. A process for activating a hydroalkylation catalyst, the process comprising:
(a) providing a hydroalkylation catalyst precursor comprising a solid acid component and a compound of a hydrogenation metal;
(b) heating the catalyst precursor at a heating rate of less than 50° C./hour in the presence of hydrogen to an activation temperature in a range from 100° C. to 260° C.; and
(c) treating the heated catalyst precursor with hydrogen in a temperature range from 50° C. below the activation temperature to the activation temperature for a duration effective to reduce at least a portion of the metal compound to an elemental form and produce an activated hydroalkylation catalyst.

E2. The process of E1, wherein the heating rate in step (b) is less than 30° C./hour.

E3. The process of E1 or E2, wherein the heating rate in step (b) is less than 20° C./hour.

E4. The process of any of E1 to E3, wherein the heating rate in step (b) is in a range from 1 to 10° C./hour.

E5. The process of any of E1 to E4, wherein the activation temperature is less than or equal to 240° C.

E6. The process of any of E1 to E5, wherein the activation temperature is in a range from 100° C. to 240° C.

E7. The process of any of E1 to E6, wherein hydrogen is supplied during steps (b) and (c) at a GHSV of less than 1000 hour$^{-1}$.

E8. The process of any of E1 to E7, wherein hydrogen is supplied during steps (b) and (c) at a GHSV of less than 250 hour$^{-1}$.

E9. The process of any of E1 to E8, wherein the treating step (c) is conducted at a hydrogen partial pressure in a range from about 10 kPa to about 10,000 kPa.

E10. The process of any of E1 to E9, wherein the treating step (c) is conducted at a hydrogen partial pressure in a range from about 100 kPa to about 2,000 kPa.

E11. The process of any of E1 to E10, wherein the duration in the treating step (c) is up to 24 hours.

E12. The process of any of E1 to E11, wherein the duration in the treating step (c) is in a range from about 0.5 hour to about 24 hours.

E13. The process of any of E1 to E12, wherein the hydrogenation metal comprises at least one of Re, Fe, Ru, Os, Co, Rh, Ir, Ni, Pd and Pt.

E14. The process of any of E1 to E13, wherein the hydrogenation metal comprises palladium.

E15. The process of any of E1 to E14, wherein the solid acid component comprises a molecular sieve.

E16. The process of E15, wherein the molecular sieve comprises a molecular sieve of MWW framework type.

E17. A process for producing a cycloalkylaromatic compound, the process comprising:
(a) providing a hydroalkylation catalyst precursor comprising a solid acid component and a compound of a hydrogenation metal;
(b) heating the catalyst precursor at a heating rate of less than 50° C./hour in the presence of hydrogen to an activation temperature in a range from 100° C. to 260° C.;
(c) treating the heated catalyst precursor with hydrogen in a range from 50° C. below the activation temperature to the activation temperature for a duration effective to reduce at least a portion of the metal compound to an elemental form and produce an activated hydroalkylation catalyst; and
(d) contacting the activated hydroalkylation catalyst in a hydroalkylation reactor with an aromatic compound and hydrogen under hydroalkylation conditions effective to convert at least part of the aromatic compound to a cycloalkylaromatic compound.

E18. The process of E17, wherein the heating step (b) and treating step (c) are conducted in the hydroalkylation reactor.

E19. The process of E17 or E18, wherein the heating rate in step (b) is less than 30° C./hour.

E20. The process of any of E17 to E19, wherein the heating rate in step (b) is less than 20° C./hour.

E21. The process of any of E11 to E20, wherein the heating rate in step (b) is in a range from 1 to 10° C./hour.

E22. The process of any of E17 to E21, wherein the activation temperature is less than or equal to 240° C.

E23. The process of any of E17 to E22, wherein the activation temperature is in a range from 100° C. to 240° C.

E24. The process of any of E17 to E23, wherein hydrogen is supplied during steps (b) and (c) at a GHSV of less than 1000 hour$^{-1}$.

E25. The process of any of E17 to E24, wherein hydrogen is supplied during steps (b) and (c) at a GHSV of less than 250 hour$^{-1}$.

E26. The process of any of E17 to E25, wherein the treating step (c) is conducted at a hydrogen partial pressure in a range from about 10 kPa to about 10,000 kPa.

E27. The process of any of E17 to E26, wherein the treating step (c) is conducted at a hydrogen partial pressure in a range from about 100 kPa to about 2,000 kPa.

E28. The process of any of E17 to E27, wherein the duration in the treating step (c) is up to 24 hours.

E29. The process of any of E17 to E28, wherein the duration in the treating step (c) is in a range from about 0.5 to about 24 hours.

E30. The process of any of E11 to E29, wherein the hydrogenation metal comprises at least one of Re, Fe, Ru, Os, Co, Rh, Ir, Ni, Pd and Pt.

E31. The process of any of E17 to E30, wherein the hydrogenation metal comprises palladium.

E32. The process of any of E17 to E31, wherein the solid acid component comprises a molecular sieve.

E33. The process of E32, wherein the molecular sieve comprises a molecular sieve of MWW framework type.

E34. The process of any of E17 to E33, wherein the aromatic compound is benzene and the cycloalkylaromatic compound is cyclohexylbenzene.

E35. A process for producing a phenol and cyclohexanone, the process comprising:
- (a1) providing a hydroalkylation catalyst precursor comprising a solid acid component and a compound of a hydrogenation metal;
- (a2) heating the catalyst precursor at a heating rate of less than 50° C./hour in the presence of hydrogen to an activation temperature in a range from 100° C. to 260° C.;
- (a3) treating the heated catalyst precursor with hydrogen in a temperature range from 50° C. below the activation temperature to the activation temperature for a duration to at least reduce a portion of the metal compound to an elemental form;
- (a) contacting benzene and hydrogen with a catalyst prepared by a process comprising steps (a1) to (a3) in a hydroalkylation reactor under hydroalkylation conditions effective to convert at least part of the benzene to cyclohexylbenzene;
- (b) oxidizing at least part of the cyclohexylbenzene produced in step (a) to produce cyclohexylbenzene hydroperoxide; and
- (c) cleaving at least part of the cyclohexylbenzene hydroperoxide produced in step (b) to produce phenol and cyclohexanone.

E36. The process of E35, wherein the heating rate in step (a2) is less than 30° C./hour.

E37. The process of E35 or E36, wherein the heating rate in step (a2) is in a range from 1 to 10° C./hour.

E38. The process of any of E35 to E37, wherein the activation temperature is in a range from 100° C. to 240° C.

E39. The process of any of E35 to E38, wherein hydrogen is supplied during steps (a2) and (a3) at a GHSV of less than 250 hour$^{-1}$.

E40. The process of any of E35 to E39, wherein the duration in step (a3) is up to 24 hours.

The invention claimed is:

1. A process for activating a hydroalkylation catalyst, the process comprising:
- (a) providing a hydroalkylation catalyst precursor comprising a solid acid component and a compound of a hydrogenation metal;
- (b) heating the catalyst precursor at a heating rate of less than 50° C./hour in the presence of hydrogen to an activation temperature in a range from 100° C. to 260° C.; and
- (c) treating the heated catalyst precursor with hydrogen in a temperature range from 50° C. below the activation temperature to the activation temperature for a duration to reduce at least a portion of the metal compound to an elemental form.

2. The process of claim 1, wherein the heating rate is less than 30° C./hour.

3. The process of claim 2, wherein the heating rate is in a range from 1° C./hour to 10° C./hour.

4. The process of claim 1, wherein the activation temperature is in a range from 100° C. to 240° C.

5. The process of claim 1, wherein hydrogen is supplied during steps (b) and (c) at a GHSV of less than 250 hour$^{-1}$.

6. The process of claim 1, wherein the treating step (c) is conducted at a hydrogen partial pressure in a range from about 10 kPa to about 10,000 kPa.

7. The process of claim 1, wherein the duration of step (c) is in a range from 0.5 hour to 24 hours.

8. The process of claim 1, wherein the hydrogenation metal comprises at least one of Re, Fe, Ru, Os, Co, Rh, Ir, Ni, Pd, and Pt.

9. The process of claim 1, wherein the solid acid component comprises a molecular sieve.

10. The process of claim 9, wherein the molecular sieve comprises a molecular sieve of the MWW framework type.

11. A process for producing a cycloalkylaromatic compound, the process comprising:
contacting an aromatic compound and hydrogen with a catalyst prepared using a process according to claim 1 in a hydroalkylation reactor under hydroalkylation conditions effective to convert at least part of the aromatic compound to a cycloalkylaromatic compound.

12. A process for producing a phenol and/or cyclohexanone, the process comprising:
- (a1) providing a hydroalkylation catalyst precursor comprising a solid acid component and a compound of a hydrogenation metal;
- (a2) heating the catalyst precursor at a heating rate of less than 50° C./hour in the presence of hydrogen to an activation temperature in a range from 100° C. to 260° C.;
- (a3) treating the heated catalyst precursor with hydrogen in a temperature range from 50° C. below the activation temperature to the activation temperature for a duration to reduce at least a portion of the metal compound to an elemental form;
- (a) contacting benzene and hydrogen with a catalyst prepared by a process comprising steps (a1) to (a3) in a hydroalkylation reactor under hydroalkylation conditions effective to convert at least part of the benzene to cyclohexylbenzene;
- (b) oxidizing at least part of the cyclohexylbenzene produced in step (a) to produce cyclohexylbenzene hydroperoxide; and
- (c) cleaving at least part of the cyclohexylbenzene hydroperoxide produced in step (b) to produce phenol and cyclohexanone.

13. The process of claim 12, wherein the heating rate in step (a2) is less than 30° C./hour.

14. The process of claim 13, wherein the heating rate in step (a2) is in a range from 1° C./hour to 10° C./hour.

15. The process of claim 12, wherein the activation temperature is in a range from 100° C. to 240° C.

16. The process of claim 12, wherein hydrogen is supplied during steps (a2) and (a3) at a GHSV of less than 250 hour$^{-1}$.

17. The process of claim 12, wherein the duration of step (a3) is in a range from 0.5 hour to 24 hours.

* * * * *